US010948499B2

(12) United States Patent
Huelsemann et al.

(10) Patent No.: US 10,948,499 B2
(45) Date of Patent: Mar. 16, 2021

(54) METHOD FOR PRODUCING A STANDARD FOR DETECTING PROTEIN AGGREGATES OF A PROTEIN MISFOLDING DISEASE, STANDARD AND USE THEREOF

(71) Applicant: Forschungszentrum Juelich GmbH, Juelich (DE)

(72) Inventors: Maren Huelsemann, Dinslaken (DE); Christian Zafiu, Aachen (DE); Oliver Bannach, Duesseldorf (DE); Dieter Willbold, Juelich (DE)

(73) Assignee: Forschungszentrum Juelich GmbH

( * ) Notice: Subject to any disclaimer, the term of this patent is extended or adjusted under 35 U.S.C. 154(b) by 261 days.

(21) Appl. No.: 15/548,266

(22) PCT Filed: Feb. 25, 2016

(86) PCT No.: PCT/DE2016/000081
§ 371 (c)(1),
(2) Date: Aug. 2, 2017

(87) PCT Pub. No.: WO2016/146093
PCT Pub. Date: Sep. 22, 2016

(65) Prior Publication Data
US 2018/0017579 A1 Jan. 18, 2018

(30) Foreign Application Priority Data
Mar. 18, 2015 (DE) ...................... 10 2015 003 404.9

(51) Int. Cl.
*G01N 33/68* (2006.01)
*G01N 33/96* (2006.01)
*G01N 33/543* (2006.01)

(52) U.S. Cl.
CPC ... *G01N 33/6896* (2013.01); *G01N 33/54346* (2013.01); *G01N 33/96* (2013.01); *G01N 2333/4709* (2013.01); *G01N 2800/2821* (2013.01)

(58) Field of Classification Search
CPC ... G01N 2333/4709; G01N 2800/2821; G01N 33/54346; G01N 33/6896; G01N 33/96
See application file for complete search history.

(56) References Cited

U.S. PATENT DOCUMENTS

2015/0024512 A1* 1/2015 Willbold ............... C07K 16/18
436/501

FOREIGN PATENT DOCUMENTS

WO        2013/092951 A2    6/2013
WO   WO 2013/092952    *   6/2013

OTHER PUBLICATIONS

Rawat et al., "Nanocarriers: Promising Vehicle for Bioactive Drugs," Biol. Pharm. Bull., 2006, vol. 29, No. 9, pp. 1790-1798.*
Ibrahim et al., "Preparation of spherical silica nanoparticles: Stober silica," J. Amer. Sci., 2010, vol. 6, No. 11, pp. 985-989.*
Hayden et al., "Amyloid β-protein oligomers and Alzheimer's disease," Alzheimer's Res. Ther., 2013, vol. 5, No. 60, pp. 1-11.*
A printout "6-Maleimidohexanoic acid N-hydroxysuccinimide," retrieved from https://www.sigmaaldrich.com/catalog/product/sigma/m9794?lang=en&region=US on Feb. 24, 2020.*
Bart et al., "Room-temperature intermediate layer bonding for microfluidic devices," Lab Chip, 2009, vol. 9, pp. 3481-3488.*
A printout retrieved from https://en.wikipedia.org/wiki/ Proteopathy on Feb. 25, 2020.*
Kim E. Sapsford et al.; "Functionalizing Nanoparticles with Biological Molecules: Developing Chemistries that Facilitate Nanotechnology", Chemical Reviews; vol. 113, No. 3; Mar. 13, 2013; pp. 1904-2074. (submitted in 3 files due to size).
Hadas Skaat et al; "Acceleration and Inhibition of Amyloid-beta Fibril Formation by Peptide-conjugated Fluorescent-maghemite nanoparticles," Journal of Nanoparticle Research: An Interdisciplinary Forum for Nanoscale Science and Technology, Kluwer Academic Publishers, DO; vol. 13, No. 8; Feb. 19, 2011; pp. 3521-3534.
Jing Yang et al., "Detection of Amyloid Plaques Targeted by USPIO-Abeta 1-42 in Alzheimer's Disease Transgenic Mice Using Magnetic Resonance Microimaging," Neuroimage, Academic Press, Orlandlo, Pl. US; vol. 55, No. 4; Jan. 10, 2011; pp. 1600-1609.
Triulzi R C et al., "Photothermal Ablation of Amyloid Aggregates by Gold Nanoparticles," Colloids and Surfaces, B. Biointerfaces, Elsevier, Amerstdam, NL; vol. 63, No. 2; Jun. 1, 2008; pp. 200-208.
M. Julia Roberti et al.; "Quantum Dots as Ultrasensitive Nanoactuators and Sensors of Amyloid Aggregation in Live Cells," Journal of American Chemical Society; vol. 131, No. 23; Jun. 17, 2009; pp. 8102-8107.
Daekyun Lee et al.; "Ca 2+-Dependent intracellular Drug Delivery System Developed with 'Raspberry-type' Particles-on-a-particle Comprising Mesoporous Silica Core and [alpha]-synuclein-coated Gold Nanoparticles," American Chemical Society, Nano; vol. 8, No. 9; Sep. 23, 2014; pp. 8887-8895.
Sperling,R alph-Aiexander; Parak, W. J. Surface modification,functionalization and bioconjugation of colloidal inorganic nanoparticles: Philosophical Transactions of the Royal Society of London A: Mathematical, Physical and Engineering Sciences, 2010, 368. Jg., Nr. 1915, S. 1333-1383.

(Continued)

*Primary Examiner* — Galina M. Yakovleva
(74) *Attorney, Agent, or Firm* — Jordan and Koda, PLLC

(57) ABSTRACT

An inorganic nanoparticle is provided (step A) having the size of the aggregate of the protein misfolding disease. Free amino groups or free carboxyl groups are formed (step B) on the surface of the nanoparticle (for functionalizing the nanoparticle surface into an amine- or carboxy-functionalized nanoparticle. Maleinimido spacer carboxylic acid is bound to the free amino groups in step (B). Or, free carboxyl groups in step (B) are converted into NHS esters. Monomers of the protein aggregate are bound i) to the maleinimido spacer carboxylic acids by way of a sulfhydryl group at the free end of the monomers, or ii) to the NHS esters by way of the amino group at the free end of the monomer. A standard is provided for use in the detection of protein aggregates occurring with protein misfolding diseases.

1 Claim, 10 Drawing Sheets

(56) References Cited

OTHER PUBLICATIONS

Majzik, A., et al. "Functionalization of gold nanoparticles with amino acid, β-amyloid peptides and fragment." Colloids and Surfaces B: Biointerfaces 81.1 (2010): 235-2 41.
Han, Sun-Ho, et al. Effective screen for amyloid β aggregation inhibitor using v amyloid β-conjugated gold nanoparticles. International journal of nanomedicine, 2011, 6. Jg., s. 1.
Farr, Tracy D. (et al.]: Imaging early endothelial inflammation following stroke by core shell silica superparamagnetic glyconanoparticles that target selectin. In: Nano letters, vol. J 14, 2014, S. 2 130-2134.—ISSN 1530-6984.
Choithani, Jyoti; Kumar, P.; Gupta, K. C. N-(3-Triethoxysilylpropyi)-6-(N-maleimido)-hexanamide: An efficient heterobifunctional reagent for the construction of oligonucleotide microarrays. Analytical biochemistry, 2006, 357. Jg., Nr. 2, S. 240-248.
Piehler, Jacob, et al. Surface modification for direct immunoprobes. Biosensors and Bioelectronics, 1996, 11. Jg., Nr. 6, S. 579-590.
Janolino, V ioleta G.; Swaisgood, Harold E. Analysis and optimization of methods using water-soluble carbidiimide for immobilization of biochemicals to porous glass. Biotechnology and bioengineering, 1982, 24. Jg., Nr. 5, S. 1069-1080.

* cited by examiner

METHOD FOR PRODUCING A STANDARD FOR DETECTING PROTEIN AGGREGATES OF A PROTEIN MISFOLDING DISEASE, STANDARD AND USE THEREOF

The invention relates to a method for producing a standard for detecting protein aggregates of a protein misfolding disease, to the standard per se, and to the use thereof.

BACKGROUND OF THE INVENTION

The term 'protein misfolding disease' is a collective term covering diseases caused by incorrectly folded, aggregating proteins. Neurodegenerative diseases such as Alzheimer s disease (AD) and Parkinson's disease are particularly relevant from a medical point of view. The diagnosis of protein misfolding diseases is usually limited to the analysis of clinical symptoms and can be made with certainty only post mortem through the histopathological detection of protein aggregates. Biomarker-based diagnostic methods, which hold the greatest promise, directly detect the pathological protein aggregates in bodily fluids. These methods not only have to be extremely sensitive, but also must be able to distinguish monomers from aggregated protein conformations. The methods are often based on what is known as an immunoassay, which is to say on the isolation or detection of the protein aggregates by way of antigen/antibody binding. The use of an internal standard in the methods is necessary for quantitatively determining protein aggregates as biomarkers. A standard for quantifying pathogenic aggregates or oligomers of endogenous proteins characterizing a protein aggregation disease, amyloid degeneration or protein misfolding diseases is known from the publication WO 2013/092951 A2. This standard is characterized in that a polymer is constructed from polypeptide sequences which, with regard to the sequence thereof, are identical in the corresponding subregion to the endogenous proteins, or show a homology of at least 50%, over the corresponding subregion, with endogenous proteins that characterize a protein aggregation disease, amyloid degeneration or a protein misfolding disease, wherein the polymers do not aggregate. The number of epitopes is determined by using a polypeptide sequence that, with regard to the sequence thereof, is identical to the subregion of the endogenous proteins which forms an epitope, or shows a homology of at least 50% with this subregion, and thus possesses the biological activity of the epitope. A polypeptide sequence thus selected is incorporated in the desired number during the construction of P1 standard according to the invention and/or linked together according to the invention. This standard is suitable for determining the actual number of pathogenic aggregates or oligomers.

The disadvantage of this standard is that the use thereof is limited.

Furthermore, it is possible to produce aggregate standards from recombinant or synthetic Aβ. The aggregation of Aβ is induced under suitable buffer conditions. The various aggregate species can then be purified using special centrifugation and chromatography techniques. So as to also stabilize the aggregates, methods for chemical cross-linking may additionally be used, such as the so-called GraFix method (Kastner et al. 2008, Stark 2010).

The disadvantage of all existing standards for determining pathological protein aggregates and oligomers occurring with protein misfolding disease is thus the limited use thereof.

SUMMARY OF THE INVENTION

It is the object of the invention to provide a standard that does not present the disadvantages of the prior art and that can be universally used over long terms, and in particular as a standard for detecting different protein misfolding diseases. It is a further object of the invention to provide a method for producing the standard and to provide advantageous uses of the standard.

The object of the invention is achieved by the method for producing the standard according to the main claim, and by the standard per se and the use of the standard according to the additional independent claims. Advantageous embodiments will be apparent from the dependent claims.

The method according to the invention for producing a standard for detecting protein aggregates of a protein misfolding disease comprises the following steps:
A) providing an inorganic nanoparticle having the size of the aggregate of the protein misfolding disease;
B) forming free amino groups or free carboxyl groups on the surface of the nanoparticle (for functionalizing the nanoparticle surface into an amine- or carboxy-functionalized nanoparticle):
C) i) binding maleinimido spacer carboxylic, acid to the free amino groups in step B), or
   ii) converting the free carboxyl groups in step B) into NHS esters:
D) binding monomers of the protein aggregate
   i) to the maleinimido spacer carboxylic acids by way of a sulfhydryl group at the free end of the monomers, or
   ii) to the NHS esters by way of the amino group at the free end of the monomer.

For step A), the nanoparticle can advantageously be oxidized since the hydroxyl groups (OH groups) form good starting points for the subsequent synthesis steps.

In one embodiment of the invention, a Stöber process for synthesis can be carried out in step A) to produce a silica nanoparticle. The Stöber process advantageously allows nanoparticles having a defined size to be produced.

The size of the produced standards is substantially determined by the size of the protein aggregates to be detected. This advantageously causes the standard to have the same size as the protein aggregate to be detected in an unknown sample. The sample is at least partially analyzed outside the human or animal body.

If a silica nanoparticle is present at least in the form of an outer shell of a nanoparticle according to the invention, silanization of the surface may be carried out in step B) in a further embodiment of the invention, using, for example, aminopropyltriethoxysilane in ethanol to form free amino groups.

In a further embodiment of the invention, amino groups are reacted with succinic acid anhydride in step B) to form free carboxyl groups. Free carboxyl groups, however, can also be produced in another manner.

In a further embodiment of the invention, a maleinimido spacer carboxylic acid is converted into an NHS, ester before being bound in step C) i) to the free amino group from step B). The reaction step is important, since the free carboxyl group is otherwise converted into an NHS ester in step C) ii).

In step C) of the method, the surface of the nanoparticle is activated. In contrast to what is customary in the prior art, it is important to take the peculiarities of the protein aggregates of protein misfolding diseases into consideration in the production of the standard. The activation of the nanoparticle itself therefore must take place prior to adding the monomers or epitopes. As an example: The $A\beta_{1-42}$ monomer comprises a known amino acid sequence. The same also applies to other monomers and proteins that play a rote in protein misfolding diseases. In the case of $A\beta_{1-42}$, it is known, for example, that the epitope region for the antibodies used is located in the region of amino acids 1-11 after the free amino group, and not in the region responsible for the aggregation. If the monomers were activated, the risk of the monomers reacting among one another and aggregating, before they can be arranged on the surface of the nanoparticle, would be significant. This information applies analogously to all other known monomers and proteins of protein misfolding diseases, see Table 1, it is therefore necessary to activate the surface of the nanoparticle in step C), either by carrying out step C) i) or step C) ii).

The treatment of carboxy-terminated nanoparticles with EDC/NHS causes conversion of the carboxylic acid into an NHS ester. This NHS ester reacts with primary amines on peptides to form amides, and thus binds these peptides to the particle. In the case of treatment of the peptides with EDC/NHS, in contrast, binding of peptides among one another would take place, in addition to the reaction with the particle surface.

In principle, it is possible to carry out a reaction of maleinimido spacer carboxylic acid prior to step C) i), or of the free carboxyl groups from step B) with 1-ethyl-3-(3-dimethylaminopropyl)carbodiimide and/or N-hydroxysuccinimide for the conversion into an NHS ester prior to step C) i) or in step C) ii). The formation of an NHS ester by way of synthesis is important to be able to carry out further reactions between the reactants.

In step D) then, monomers of the protein aggregate are bound
  i) to the maleinimido spacer carboxylic acids by way of a sulfhydryl group at the free end of the monomers, or
  ii) to the NHS esters by way of the amino group at the free end of the monomer.

It is not necessary to bind the complete sequences of the monomers of the protein aggregates on the surface of the nanoparticles. Rather, it may be sufficient to bind the epitope region, if this is known, to the maleinimido spacer carboxylic acids or to the NHS esters.

The term 'monomer' within the meaning of the invention thus also applies to an epitope region or, generally speaking, a recognition sequence, which is afterwards utilized during the use of the standard so as to bind a specific antibody thereto, or a peptide that detects the protein misfolding disease.

In one embodiment of the invention, the standard can also comprise several monomer types on the nanoparticle surface. This advantageously also allows standards for protein aggregates, consisting of two or more different monomers, to be produced.

In a further advantageous embodiment of the invention, a streptavidin molecule is arranged on the NHS ester of the nanoparticle after step C) ii has been carried out, and a biotin group is arranged on the monomer of the protein aggregate prior to step D). This advantageously allows monomers comprising biotin groups to be bound to particles.

However, the binding of the amino group of the monomers with the NHS ester in step D) ii) can take place covalently.

A standard for detecting protein aggregates of a protein misfolding disease is also provided by the described method, among other things. However, this may also be provided in a different manner.

According to the present invention, the free amino groups on the surface of the nanoparticles are converted into free carboxyl groups or into maleimide groups.

It shall be pointed out that the above-mentioned method refers, in particular, to the production of silica nanoparticles, without being limited thereto. It is also easily possible to provide gold particles with free amino groups or hydroxyl groups on the surface.

For gold nanoparticles, a ligand exchange reaction is employed, in which surface functionalization is performed with the appropriate thiols. It shall be mentioned that a carboxy-functionalization of the gold particles is achieved when using 3-mercaptopropionic acid, and an amino-functionalization when using 2-mercaptoethylamine. Moreover, it is possible, as will be shown hereafter, to use quantum dots as the starting material for the method.

In the lower size range of the protein aggregates, which is to say in the range of approximately 4 to 7 nm, the use of quantum dots as nanoparticles is particularly suitable. Gold nanoparticles are also suitable in the medium size range of the protein aggregates of approximately 2 to 60 nm, and plastic particles, such as latex, modified polystyrene and so forth, are suitable in the upper size range (>40 nm).

Silica nanoparticles according to the invention, serving as standards for detecting protein misfolding diseases, however, can advantageously be employed across the entire size range and can be easily produced in the manner shown.

In the case of plastic and silica nanoparticles, there is advantageously an additional option to mix these with fluorochromes or quantum dots, and, in this way, to internally mark them, so as to attain additional advantages of the standard as a quality control measure, such as in an sFIDA assay, and/or with respect to the spectroscopic properties thereof.

The silica nanoparticles according to the invention are thus composed of amorphous silicon dioxide following the Stöber process. This approach advantageously causes hydroxyl groups to be present on the surface of the silica nanoparticles.

The Stöber process can advantageously be used to synthesize particles across a wide size range, which each have a very narrow, and preferably monodisperse, size distribution. This property is particularly advantageous when using the nanoparticles as a standard.

Synthesis of Silica Nanoparticles and QD Silica Nanoparticles

In a first variant, silica nanoparticles are produced using the Stöber process for synthesis. Ethanol, water and ammonia solution are brought in contact with one another at a suitable ratio, depending on the desired size of the nanoparticle to be synthesized. Tetraethoxy orthosilicate (abbreviates as, TEOS) is added to this batch, and the Stöber process is carried out. The ratio of the solvents, catalysts and reactants to one another determines the size of the particles and is selected such that the nanoparticle has the size of the protein aggregate, such as an oligomer of the protein misfolding disease to be detected. As a result, the silica nanoparticle having the desired size of the aggregate and/or oligomer is present. Hydroxyl groups are present on the surface of the silica nanoparticle. Optionally, the catalysts are removed. For this purpose, the particle solution can be transferred into dialysis membranes, for example, and be dialyzed or centrifuged off.

In a second variant, fluorescent quantum dots (QD), preferably CdSe/ZnS, are functionalized with (3-mercaptopropyl)trimethoxysilane (MPS). Subsequent to the functionalization, these nanoparticles comprise ethoxysilane groups and tetraethoxy orthosilicate (TEOS). Such nanoparticles can be used as crystallization centers in the Stöber process to form a silicate shell having a certain size. Advantageously, silica QD particles are created, which have the fluorescent properties of the quantum dots per se. The surface of such silica QD nanoparticles likewise comprises hydroxyl groups.

The silica nanoparticles, or the QD silica nanoparticles, are then silanized, for example by way of aminopropyltriethoxysilane (abbreviates as, APTES). This advantageously causes the free amino group to be immobilized on the surface of the particles. The corresponding resulting molecule is an amino-functionalized silica nanoparticle, see [1] in FIG. 1. 3-aminopropyl silica nanoparticles or 3-aminopropyl silica QD nanoparticles are created.

In one variant of the method, succinic acid anhydride can be bound to this free amino group, whereby a carboxy-functionalized silica nanoparticle is formed. For reasons related to the reaction, this comprises a free carboxyl group, see [2] in FIG. 1.

It goes without saying that a plurality, preferably a known number, of such free amino groups or carboxyl groups are disposed on the nanoparticle surface.

Production of Quantum Dot Surface Modifications

In a further variant, quantum dots (Qdots) are used directly as the core. These are commercially available on the market. In particular, so-called core-shell quantum dots made of CdSe/ZnS, are particularly well-suited for small nanoparticles having fluorescent properties. These may be present in the range of 2 to 7 nm, for example. With increasing diameter, the fluorescence shifts from blue toward red.

In a further step according to the invention, 0.1 nM Qdots (quantum dots) is mixed with a thiol spacer acid mixture. This thiol spacer acid mixture is composed, for example, of 550 mM tetramethylammonium hydroxide, 275 mM thiol spacer acid (such as 3-mercaptopropionic acid) in 1 mL $CHCl_3$, for example, wherein the resultant aqueous phase is removed. This solution is mixed with the Qdots, and 50 µL PBS is added after 2 days. After solvent extraction, the Qdots migrate into the aqueous phase, and carboxy-functionalized Qdots are obtained.

In another variant, 1 mg dry Qdots is mixed with an amino spacer thiol mixture in methanol. This amino spacer thiol mixture is composed of 100 mg amino spacer thiol (such as 2,2'-diaminodiethyl disulfide). The mixture is sonified until the solution takes up the Qdots. These are centrifuged off and placed in water. Amino-terminated Qdots are present in the aqueous phase.

Coupling of Monomers or Epitopes or, Generally Speaking, Recognition Sequences to the Nanoparticles Nanoparticles having carboxy terminals are, as mentioned above converted into a reactive NHS ester. The NHS ester is preferably formed by way of 1-ethyl-3-(3-dimethylaminopropyl)carbodiimide (EDC for short) and/or N-hydroxysuccinimide (NHS for short). The NHS ester represents the reactive intermediate stage for the reaction with a primary amine, which is added as a monomer to the protein misfolding diseases to be detected.

A second variant of the method according to the invention provides for the amino-functionalized nanoparticle from [1] in FIG. 1 to be reacted with a maleinimido spacer carboxy, such as with 6-maleinimido caproic acid or maleinimido PEG (optional length)-COOH. The pathway is shown in FIG. 2B.

This advantageously causes a group to be introduced on the surface of the nanoparticle, the group reacting specifically with thiols.

In a third variant, the above-mentioned NHS ester particles are used to bind streptavidin on the surface of the nanoparticles, see FIG. 2C.

The nanoparticles per se, which is to say without the monomer (or epitope) of the protein aggregate, are novel and thus already achieve the object of the invention:

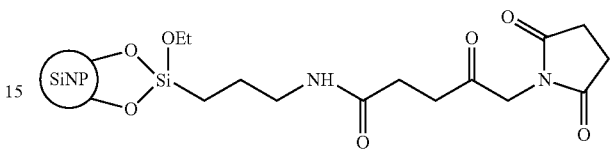

is a particularly preferred starting product comprising NHS esters on the surface of, for example, silica nanoparticles (SiNP).

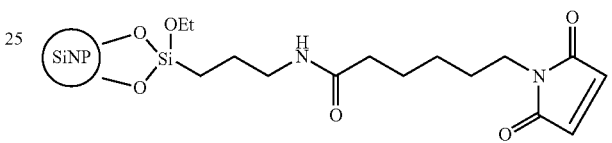

is a particularly preferred starting product comprising maleinimido groups on the surface of, for example, silica nanoparticles (SiNP).

A plurality of the compounds, which are each only shown once here, are, of course, disposed on the surface of the nanoparticles. Advantageously, this number is precisely determined by way of calculation and depends on the diameter of the particle.

The nanoparticles according to the invention are produced or provided, among other things, by the method for production according to the invention.

Nanoparticles comprising N-hydroxysiccinimide ester surfaces react with the primary amine of the monomer or of a synthetic epitope of the aggregate and/or oligomer of the protein misfolding diseases to be detected, possibly cleaving N-hydroxysuccinimide.

This method is particularly suitable when the amino acid lysine is present once or multiple times in a peptide sequence of the monomer. This method is particularly suitable when the amino acid is not present in the epitope region, which is to say the binding region for antibodies. If no lysine is present, either the N-terminus of the amino acid sequence itself may be used for binding to the nanoparticle, or the peptide sequences having additionally introduced lysines may be used.

Nanoparticles comprising maleinimido groups on the surface possibly react with existing or synthetically introduced thiols (such as cysteine) in the protein sequence of the monomer or epitope.

Nanoparticle comprising a streptavidin surface bind particularly strongly biotinylated monomers or epitopes.

The above-mentioned standards without the monomers or epitopes can be universally used in a particularly advantageous manner as a platform technology for the further production of a standard with the monomers or epitopes for the detection of protein misfolding diseases. They are provided, in particular, in kits together with the protein or monomer or epitope of the protein aggregate of the protein misfolding disease, together with a solvent.

These silica nanoparticles react with the primary amine of the monomer of the aggregate and/or oligomer of the protein misfolding diseases to be detected, possibly cleaving N-hydroxysuccinimide.

In variant 1, N-hydroxysuccinimide is cleaved during the reaction with the primary amine of the monomers, see FIGS. 2A and 2C, while in variant 2, the NHS ester remains on the silica nanoparticle, see FIG. 2B.

The further pathways of binding the monomers to the NHS esters with or without spacers are indicated in the general pathways of FIGS. 2A to 2C. These pathways describe different methods of biofunctionalization. Due to the chemical surface properties, modifications can be easily carried out. Moreover, the material is stable in physiological buffer solutions and considered to be non-hazardous to health.

In particular, the above-shown biofunctionalized silica nanoparticles according to the invention represent stable standards having an exactly defined size and comprising a number of accessible epitopes that can be precisely determined, and are therefore likewise advantageously employed as a platform technology in diagnostic testing methods or in spiking experiments for protein misfolding diseases.

An overview of the proteins or protein aggregates that occur with protein misfolding diseases is provided in Table 1. The sizes of the corresponding protein aggregates are known from the literature. By way of example, the size of the amyloid beta oligomer of Alzheimer's disease is approximately 20 nm.

Steps A) and B) of the method are carried out accordingly.

TABLE 1

| Protein and associated protein misfolding disease | |
|---|---|
| Protein monomer or epitope | Protein misfolding disease |
| Amyloid beta | Alzheimer's disease |
| Prion protein | Prion disesases |
| Serum amyloid A protein | AA amyloidosis |
| IgG light chain | AL amyloidosis |
| AapoAI | AApoAI amyloidosis |
| AapoAII | AApoAII amyloidosis |
| ATTR | ATTR amyloidosis |
| DISC1 | DISC1 opathies |
| FUS | FUS proteinopathies |
| IAPP | Diabetes Mellitus type 2 |
| SOD1 | Amyotrophic lateral sclerosis |
| α-synoclein | Synucleinopathies |
| Tau | Tauopathies |
| TDP-43 | TDP-43 proteinopathies |
| Huntingtin | Huntingon's disease |
| Lysozyme | Familial visceral amyloidosis |

The standard for detecting toxic aggregates and/or oligomers of a protein misfolding disease then comprises an inorganic nanoparticle having, disposed on the surface thereof, a certain number of binding sites for the monomers of the aggregate, or the epitope thereof, of the protein misfolding disease to be detected.

This advantageously allows the nanoparticles, including binding sites, to be utilized as a platform technology for various protein misfolding diseases.

In one embodiment of the invention, the nanoparticle loaded with monomers has a size corresponding to the aggregate and/or oligomer of the protein misfolding disease.

It was found that, in this way, particularly good imitation with respect to the size of the species occurring with protein misfolding disease is achieved.

In one embodiment of the invention, the number of the epitopes in the standard thus corresponds to the number of the monomers or epitopes present in the protein aggregate. This advantageously causes the standard to have a number of binding sites equal to that of the naturally occurring toxic aggregate and/or oligomer.

In a further advantageous embodiment of the invention, the standard has a size of 2 to 200 nm, preferably 2 to 60 nm, and particularly preferably 2 to 20 nm. In particular, a size of approximately 2 to 20 nm is also where the aggregates and/or oligomers of most protein misfolding diseases can be found. This means that this measure provides standards that have a size identical to the toxic aggregates and/or oligomers in most protein misfolding diseases.

In an especially and particularly advantageous manner, silica nanoparticles can be synthesized in a defined manner by way of the Stöber process. It is also possible to produce very small cores, in particular at a size of 2 to 20 or 25 nm. Silica nanoparticles can advantageously be produced at orders of magnitude of 1 to 200 nm, wherein they can take on any intermediate value.

The standards, however, can also comprise a gold nanoparticle or a quantum dot, serving as the core.

The standards can also comprise gold or a quantum dot, serving as the core, and be enveloped by a silicate layer.

In a particularly advantageous manner, activated NHS esters, maleinimide groups or streptavidin for binding monomers of the toxic aggregate and/or oligomer are disposed on the surface of the nanoparticle.

In a particularly advantageous manner, a certain standard comprises approximately 40 amyloid beta monomers of Alzheimer's disease, which are disposed on an NHS ester-activated surface of an approximately 25 nm large silica nanoparticle. This advantageously provides a standard that approximately has an identical size and possibly spatial structure as the toxic amyloid beta oligomer to be detected, and comprises approximately the same number of epitopes as are present in the aggregate. It was found that, in this way, a standard having a defined and similar binding capacity for antibodies as the toxic amyloid beta oligomer is provided.

It was found, within the scope of the invention, that aggregate standards produced according to the methods of the prior art have several serious disadvantages, which the standards according to the invention no longer have. Disadvantages in the prior art relate to the lack of homogeneity, for example. Since protein aggregation is a time-critical process, producing aggregates having a precise, predefined size poses a major challenge. An inhomogeneous size distribution can likewise be problematic. Previously, it has not been possible to remedy these disadvantages.

Furthermore, the lack of adaptability of the existing methods and standards is a fundamental problem in the prior art. For example, the sFIDA process can be adapted for the detection of various disease-associated protein aggregates, such as are summarized in Table 1. For every aggregate standard, however, initially suitable aggregation and purification conditions would then have to be determined using complex experimentation. At times, certain proteins do not aggregate at all in vitro, or supply only metastable intermediates, which cannot be satisfactorily isolated.

In particular, it was found that the stability of the standards according to the prior art is not sufficient, and that the use of the standards is therefore limited in terms of time. In particular, the standards according to the prior art can aggregate further after purification and during storage, which has an undesirable effect on the size distribution.

It was furthermore found within the scope of the invention that the accessibility of the epitope is not sufficient in the prior art. In the case of larger protein aggregates, it is difficult to quantify the number of epitopes accessible for antibody binding, even if the exact number of monomeric subunits is known.

Furthermore, it was found that the standards according to the prior art also limit the selection of the protein sequences, resulting again in limited use of these standards. The protein sequence must include at least both the hydrophobic region responsible for aggregation, and the epitope for antibody binding.

For the reasons cited, it is evident that the standards according to the prior art are uneconomical in terms of production and usability. In most instances, expensive proteins are used to produce the aggregates, even though only the surface is ultimately needed.

In the present case, inexpensive inorganic nanoparticles are thus also used as a standard base.

Moreover, time-intensive and cost-intensive methods (such as chromatographic methods) for purifying the product are required for the standards in the prior art due to the inhomogeneous size distribution.

In addition, the use of the standards according to the prior art is also limited in terms of function. The lack of a marking option with the standards according to the prior art, for example, is a problem. In the case of homogeneous aggregates, it is often possible for desired chemical modifications (such as fluorescent markers) to adversely affect the properties, such as the accessibility of the epitope.

The standards according to the invention do not have the above-described drawbacks. Rather, standards according to the invention have a narrow size distribution and allow surface modification for bioconjugation. Additionally, these are water-soluble in the desired size range. They can be stored for longer periods, without losing the desired properties as a standard, in particular for a platform technology.

BRIEF DESCRIPTION OF THE DRAWINGS

The invention will be described in more detail hereafter based on exemplary embodiments and the accompanying figures, without thereby limiting the invention.

DESCRIPTION OF THE PREFERRED EMBODIMENTS

Figure 1:
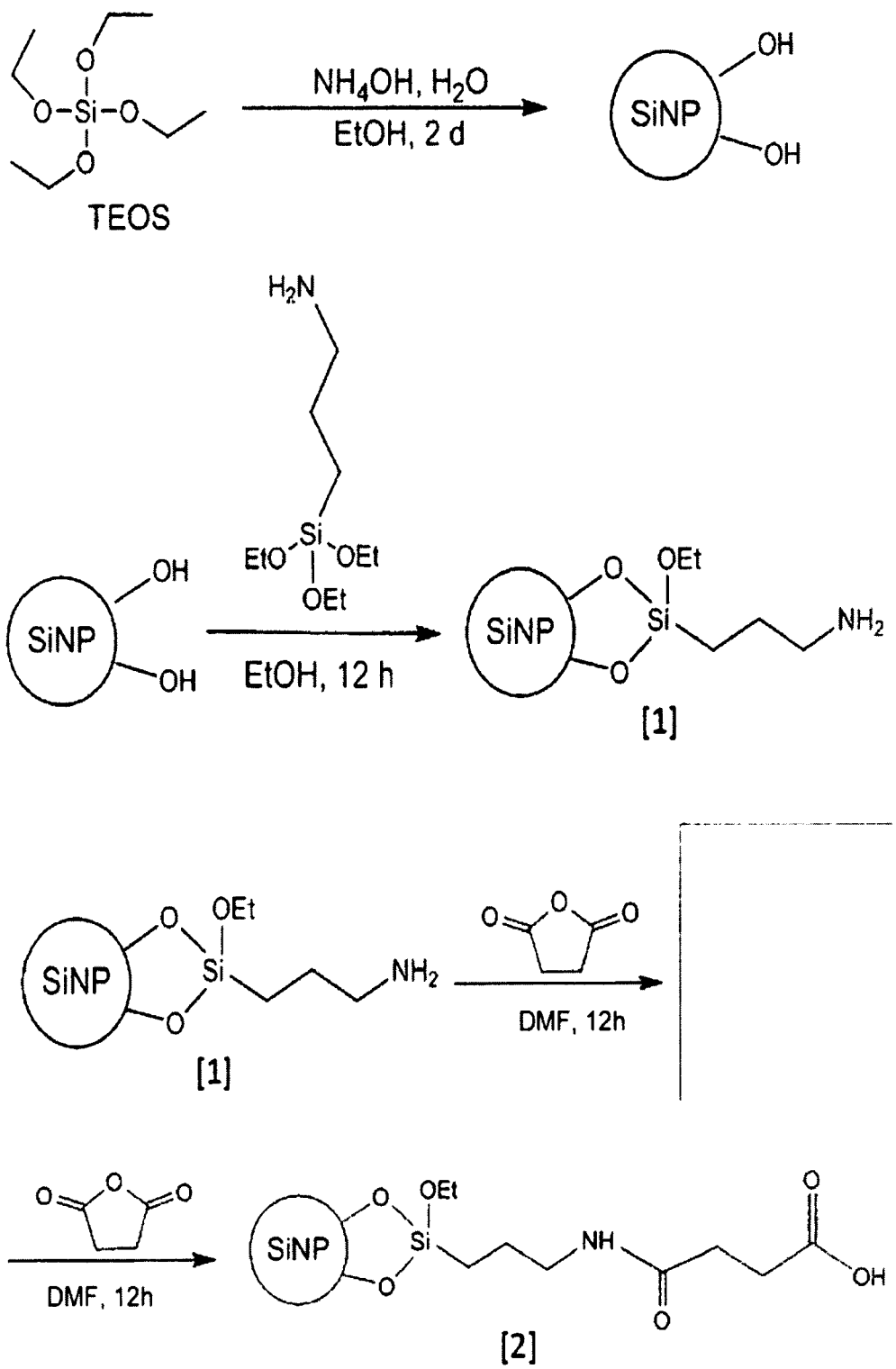
FIG. 1 shows the production of silica nanoparticles bases as a platform technology.

FIGS. 1 and 2 show the production of silica nanoparticles. Production of Silica Nanoparticles Production based on amyloid β silica nanoparticles (Aβ SiNPs) for use in the diagnosis of Alzheimer's will be described hereafter:

I. General Synthesis of SiNPs:
1. Silica nanoparticles having a diameter of 20 nm are produced, since natural toxic Aβ oligomers also have approximately this size.

To this end, ethanol, water and ammonia solution are added at a suitable ratio (depending on the desired size) into a glass flask and stirred vigorously. After two minutes, TEOS (triethoxy orthosilicate) is added. The solution is stirred for two days at room temperature (Stöber process for synthesis). For 20 nm SiNP, 200 ml ethanol (99%). 27 mL water (deionized) and 4.47 mL ammonia (30%) are stirred and mixed with 4:43 mL TEOS. The reaction was carried out at room temperature for 2 days while stirring vigorously.

2. The particle solution is transferred into dialysis membranes (MWCO 3500) and dialyzed for two days against ethanol so as to remove excess reactants and the catalyst, 3. For silanization, aminopropyltriethoxysilane is added to the SiNPs in ethanol so as to immobilize a free amino group on the particle surface. Aminopropyltriethoxylane is added at a quintuple excess in relation to the spatially possible number of binding aminopropyltriethoxysilane molecules. The next day, the excess aminopropyltriethoxysilane is removed by way of three centrifugation and washing steps, with ethanol. The pellet must be sonified for at least 20 minutes after every centrifugation step (3000 g, minimum of 2 hours) so as to separate the particles again.

In the case of 20 nm SINP, 120 μL APTES is admixed to 50 mL SiNP solution (10 g $l^{-1}$) in ethanol and stirred over night.

A variety of pathways of biofunctionalization may be employed. The following pathways shall be described in more detail only by way of example, which is to say without being limiting in any way.

A. Modification Using Amyloid Beta Oligomer 1-42 and 2-MAP Peptides, FIGS. 1, 2A 4A. In the next step, a carboxyl group is applied to the particle surface by reacting the amino group with succinic acid anhydride. For this purpose, the particle pellet is dissolved under an argon atmosphere in 0.1 M succinic acid anhydride in DMF, sonified for 20 minutes, and subsequently stirred overnight under an argon atmosphere at room temperature. The next day, the DMF solution is replaced with ethanol by way of three centrifugation and washing steps (3000 g, at least 2 hours) with ethanol. The pellet must be sonified for at least 30 minutes after every centrifugation step so as to separate the particles again.

In the case of 20 nm SiNP, 500 mg aminated SiNP (from step 3A) in 50 mL of a 0.1 M succinic acid anhydride solution in DMF is stirred overnight.

Figure 2A:
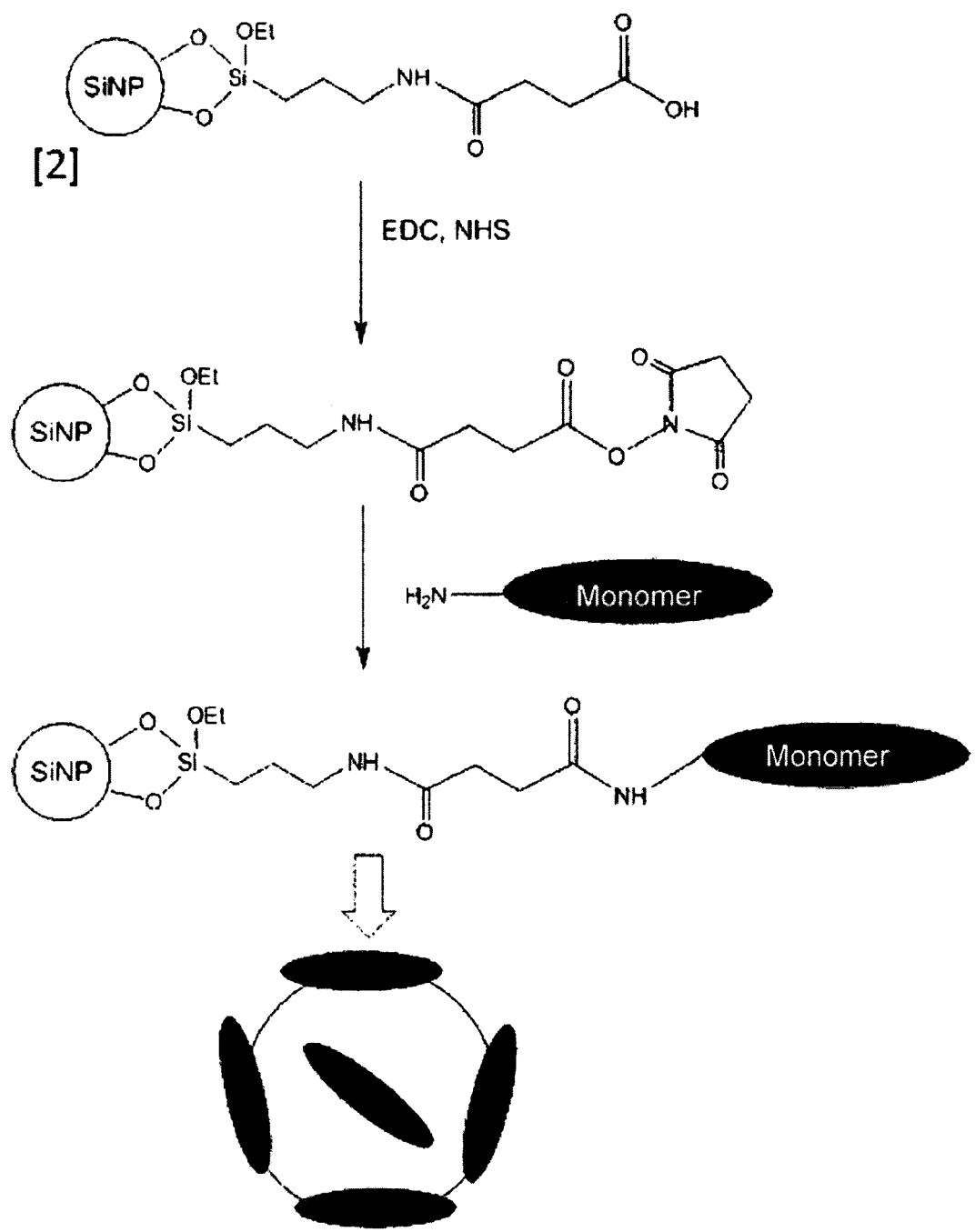
FIG. 2A shows the production of a silica nanoparticle according to a first variant.

In this way, the nanoparticle according to [2] is provided (cSiNP). The steps according to FIG. 2A are thus carried out.

5A. The introduced carboxyl group is converted into a NHS ester by way of a reaction with 1-ethyl-3-(3-dimethylaminopropyl)carbodiimide and N-hydroxysuccinimide, the NHS ester representing a reactive intermediate stage to the reaction with a primary amine. For this purpose, the particle pellet is placed in 10 mM MES buffer (2-(N-morpholino)ethanesulfonic acid), and 1-ethyl-3-(3-dimethylaminopropyl)carbodiimide and N-hydroxysuccinimide are added at a ratio of 4:1 to the anticipated carboxyl groups on the surface of the particle. The 1-ethyl-3-(3-dimethylaminopropyl)carbodiimide/N-hydroxysuccinimide activation is used to couple proteins, since these have a primary amino group at the N-terminus, or primary amines are present in the side chains (such as lysine).

6A. In the next step, the activated particles are added to the respective biomolecule, or vice versa. As mentioned, a variety of potential biomarkers or other peptides may be used here. In this specific example, $A\beta_{1-42}$ peptides and/or 2-MAP peptides, the latter consisting of two coupled Aβ 1-11 units, were covalently bound to the activated binding sites on the silica nanoparticles. So as to prevent cross-linking of the peptides among one another, the excess of 1-ethyl-3-(3-dimethylaminopropyl)carbodiimide and N-hydroxysuccinimide was first removed. This is achieved by way of two centrifugation and washing steps (3000 g, 0.5 hour) against 10 mM MES buffer. The reaction step is time-critical and should be carried out within 2 to 3 hours.

7A. The activated particles are placed in 10 mM MES buffer to the corresponding dry peptide aliquots evaporated from hexafluoroisopropanol (HFIP), yielding an approximate ratio of 5:1 of potentially free binding sites to the peptide, since one peptide is spatially able to bind to approximately every tenth binding site (calculated for a diameter of 20 nm).

The mixture is sonified for 30 minutes, whereby the protein film detaches from the vessel wall, and is incubated over night while shaking at room temperature.

8A. So as to remove non-bound peptides, the particles are centrifuged the following day, placed HFIP, and sonified for 30 minutes. After 2 further centrifugation and washing steps in water, the biofunctionalized silica nanoparticles (in the example, $A\beta_{1-42}$ SiNP or 2-MAP SiNP) are present in water and can be stored at 4° C. until further use.

Figure 2B:
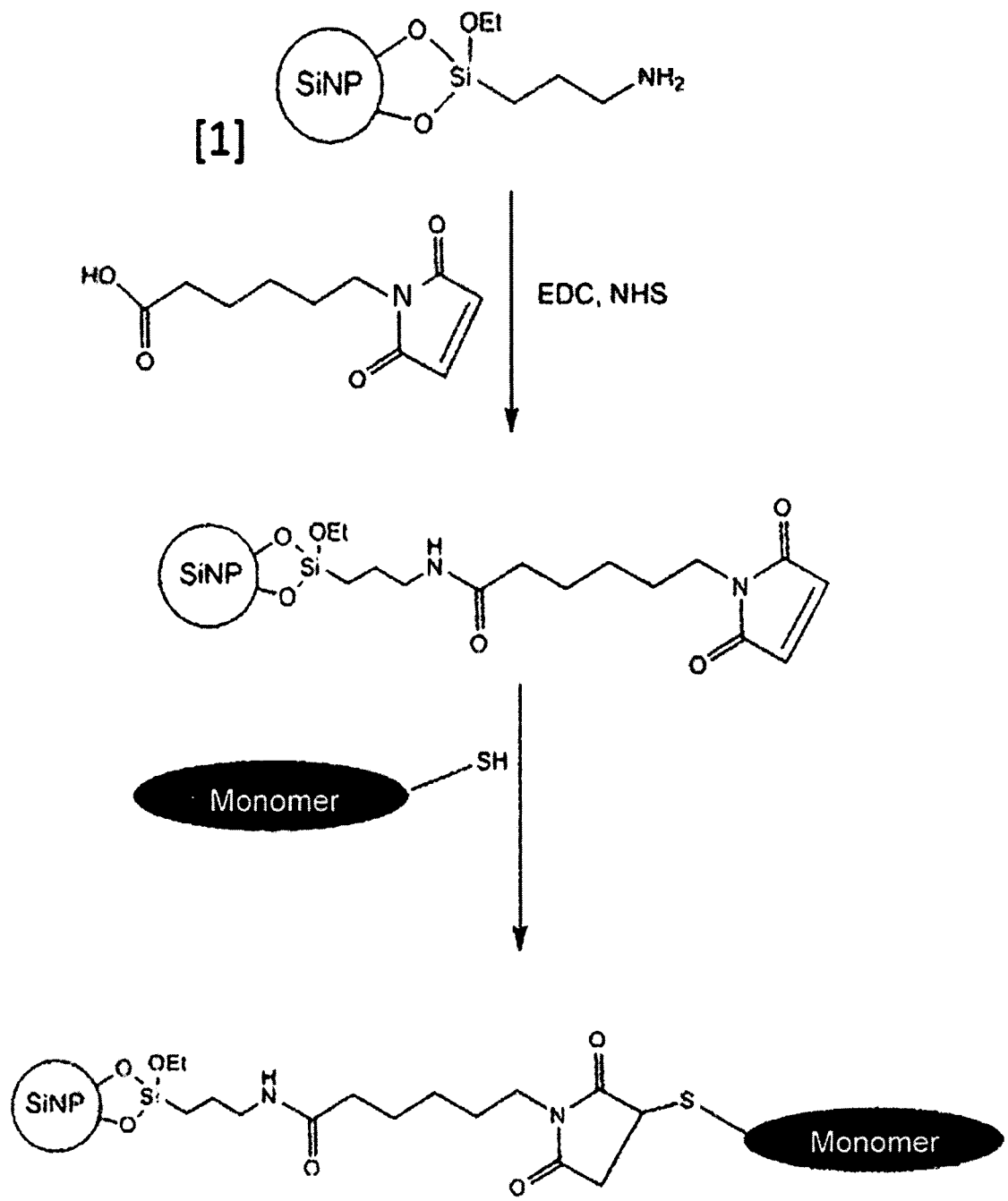
FIG. 2B shows the production of a silica nanoparticle according to a second variant.

B. Covalent Modification Using Synthetic Epitopes (Oligo Peptides) (FIGS. 1, 2B)

Step 4B is performed instead of step 4A from A. Aminated silica nanoparticles, see [1] in FIGS. 1 and 2B, from general step 3 are transferred into PBS. This is achieved by way of centrifugation (3000 g, 20 minutes, 25° C.) and washing twice with PBS. The nanoparticles are dispersed again by way of treatment in an ultrasonic bath.

5B. A biofunctional molecule maleinimido spacer carboxylic acid, such as 6-maleinimido caproic acid here, is dissolved in DMF or water and mixed with EDC and NHS at a ratio of 1:4:1 in PBS and stirred for 30 minutes at room temperature so as to convert the carboxylic acid into a reactive NHS ester.

5B. This reaction mixture is added to the aminated silica nanoparticles from general step 3, and more specifically at a quintuple molar excess in relation to the amine groups present. At a diameter of 20 nm, approximately 2095 primary amine groups are present on the silica nanoparticle. The reaction solution is stirred for one hour at room temperature.

7B. The reaction is stopped by way of ethanolamine in the same concentration as NHS.

8B. The corresponding synthetic epitope as Ab 1-11+SH), which is provided with a terminal cysteine or cystamine, is dissolved in a 20 mM TCEP (tris(2-carboxyethyl)phosphine) solution in PBS and incubated for 1 hour. TCEP causes potential disulfides to be reduced to thiols. This solution is now added at a molar ratio of 1:1 of the epitope to the possible surface sites (20 nm: 2095) of the particles to be functionalized. The reaction is carried out overnight (approximately 8 hours) while stirring.

9B. The purification takes place by way of dialysis (dialysis membranes MWCO 3500) against PBS, or by way of centrifugation (3000 g, at least 2 hours) with 2 PBS washing steps.

It goes without saying that, at the end of the reaction pathway of FIG. 25, a schematic spherical nanoparticle, which for space reasons is not shown, is present as the standard, analogously to the end product of FIG. 2A.

C. Non-Covalent Modification Using Synthetic Epitopes (Oligopeptides), FIGS. 1, 2C Subsequent to general steps 1 to 3 and 4A, 5A and 6A from A, step 7C is performed instead of step 7A from A. The activated particles from step 6A are mixed in 10 mM MES buffer with streptavidin in PBS, yielding an approximate ratio of 20:1 of potentially free binding sites to the peptide, since one streptavidin is spatially able to bind to approximately every fortieth binding site (calculated for a diameter of 20 nm), see FIG. 2C.

8C. After two hours, the reaction is quenched with ethanolamine in PBS using the same molar ratio as NHS. Thereafter, the mixture is dialyzed against PBS (MWCO 3500) or centrifuged (3000 g. at least 2 hours) and washed twice with PBS 9C. The corresponding biotinylated oligopeptide (or epitope, see FIG. 2C, biotin group as a blank triangle) is dissolved in PBS and mixed at a ratio of 1:1 (in relation to the theoretically bound streptavidin count) with the functionalized SiNP and stirred for 2 hours.

10C. The particles are centrifuged (3000 g. at least 2 hours) and washed twice with PBS.

Figure 2C:
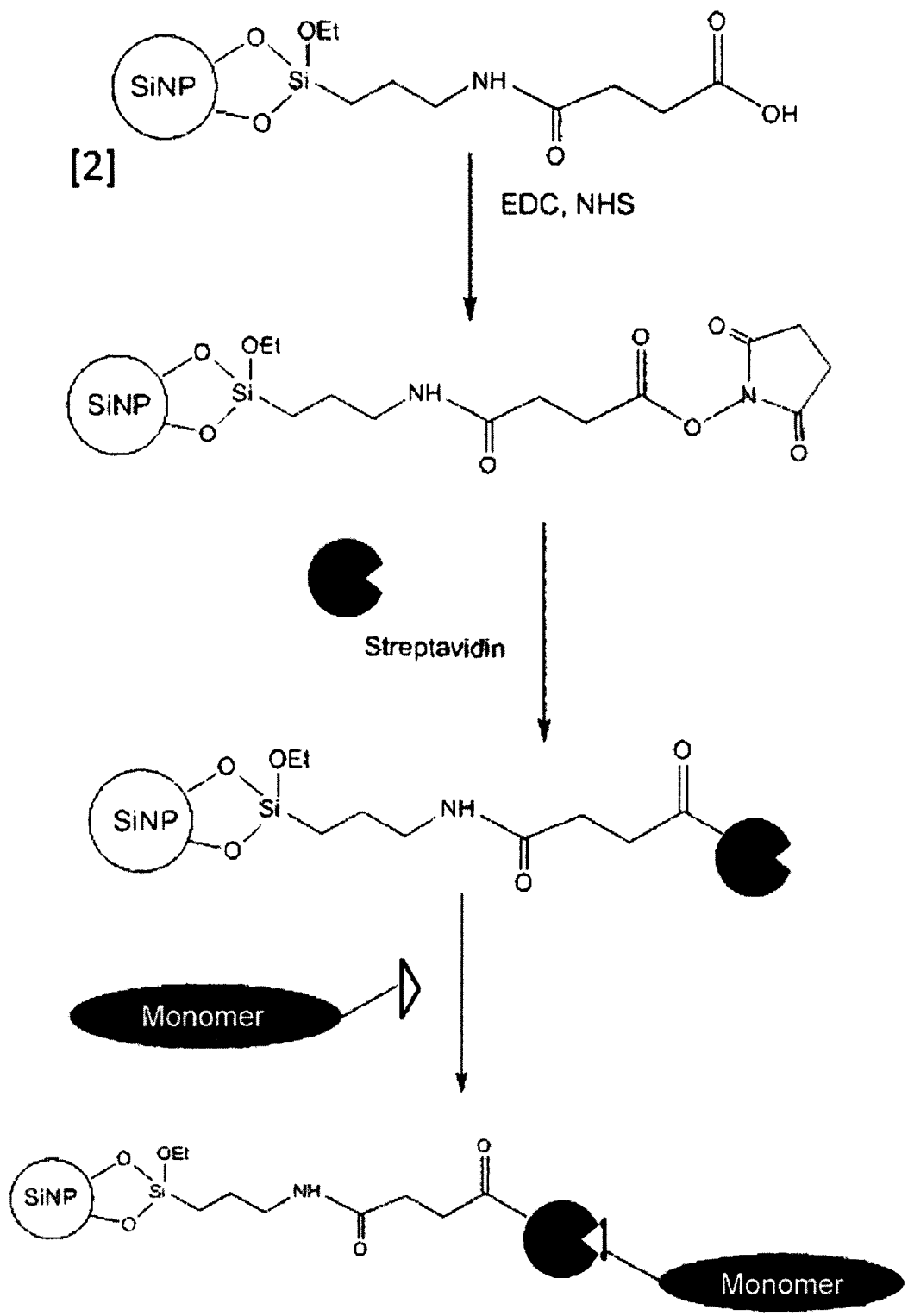
FIG. 2C shows the production of a silica nanoparticle according to a third variant.

It goes without saying that, at the end of the reaction pathway of FIG. 2C, a schematic spherical nanoparticle, which for space reasons is not shown, is present as the standard, analogously to the end, product of FIG. 2A.

Analyses:

The particle characterization (size, homogeneity, hydrodynamic radius) is performed based on transmission electron microscopy (TEM) and dynamic light scattering (DLS) images.

The concentration of the particles can be determined gravimetrically after every step by removing the solvent in the concentrator and by way of calculation based on the known size.

The successful functionalization steps are recorded by way of FTIR spectra (Fourier transform infrared spectroscopy).

The number of peptides can be ascertained as follows, for example:

The activated particles are functionalized with cysteine Aβ. This introduces a thiol group for each bound peptide, which can be detected by way of a stoichiometric 1:1 reaction with Ellman's reagent. Here, the thiol from the cysteine reacts with DTNB (5,5'-dithiobis-(2-nitrobenzoic acid); Ellman's reagent), releasing 2-nitro-5-thiobenzoate (TNB-), which can be deprotonated to yield the yellow dye TNB2- and quantified, using a wavelength of 412 nm.

Figure 3:
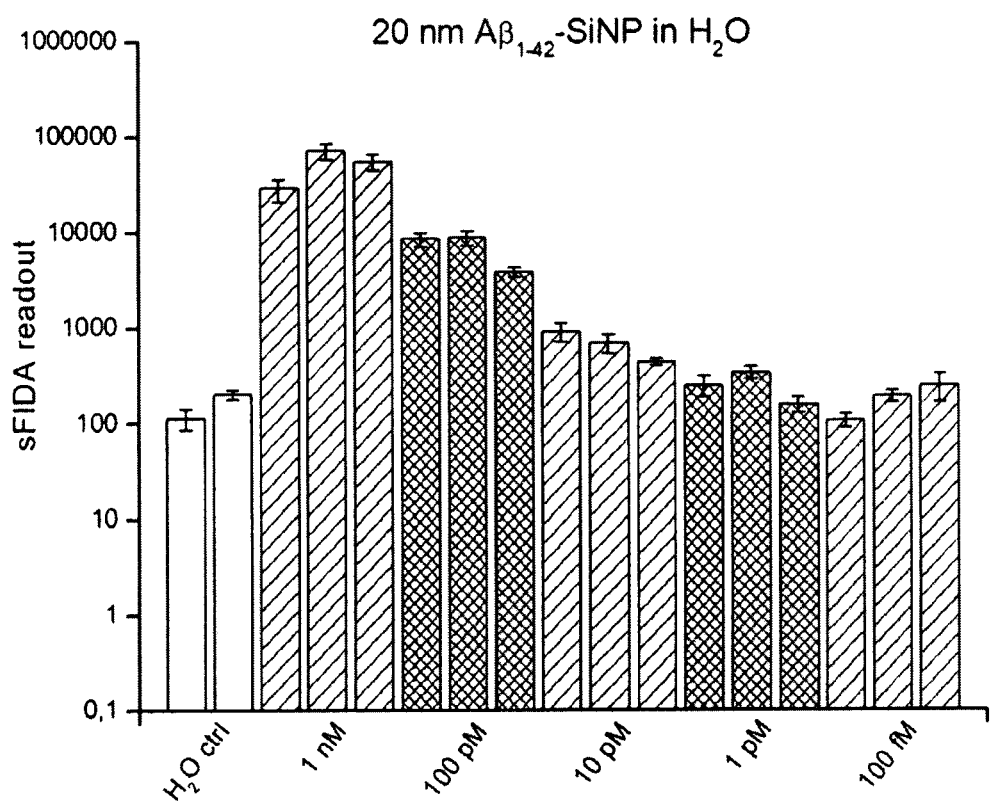
FIG. 3 shows a sFIDA readout for 20 nm $A\beta_{1\text{-}42}$ SiNP, which were diluted in $H_2O$ from 1 nM to 100 fM.

Results:

FIG. 3 shows the sFIDA readout for 20 nm $A\beta_{1-42}$ SiNP, which were diluted in $H_2O$ from 1 nM to 1 fM. The samples were measured in the sFIDA using triple determination.

A clear concentration dependence of the sFIDA readout is evident.

Figure 4:
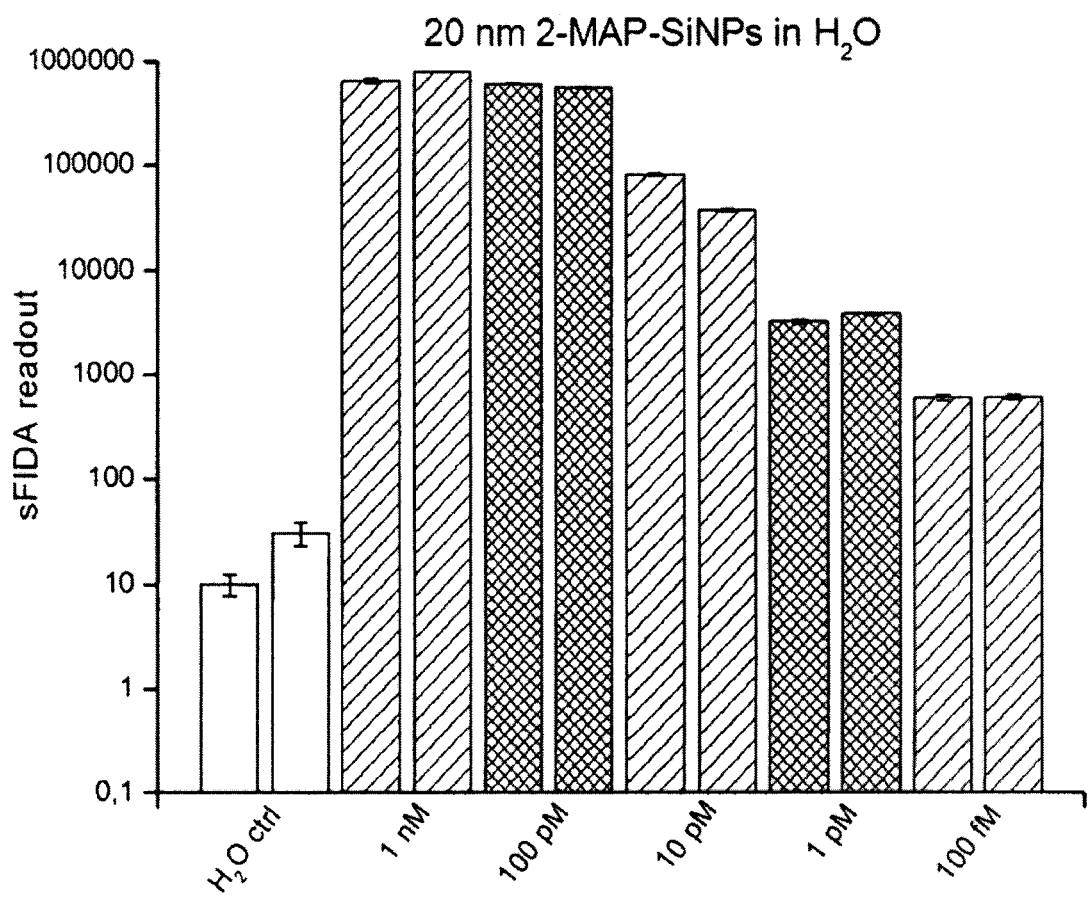
FIG. 4 shows a sFIDA readout for 20 nm 2-MAP SiNP, which were diluted in $H_2O$ from 1 nM to 100 fM (the 2-MAP molecule consists of two $A\beta_{1\text{-}11}$ sub-units coupled to one another)

FIG. 4 shows the sFIDA readout for 20 nm 2-MAP SiNP, which were diluted in $H_2O$ from 1 nM to 1 fM (the 2-MAP molecule consists of two $A\beta_{1-11}$ sub-units coupled to one another).

The samples were measured in the sFIDA using double determination. A clear concentration dependence of the sFIDA readout and a clear delimitation of the $H_2O$ control to the lowest femtomolar range are evident.

Figure 5:
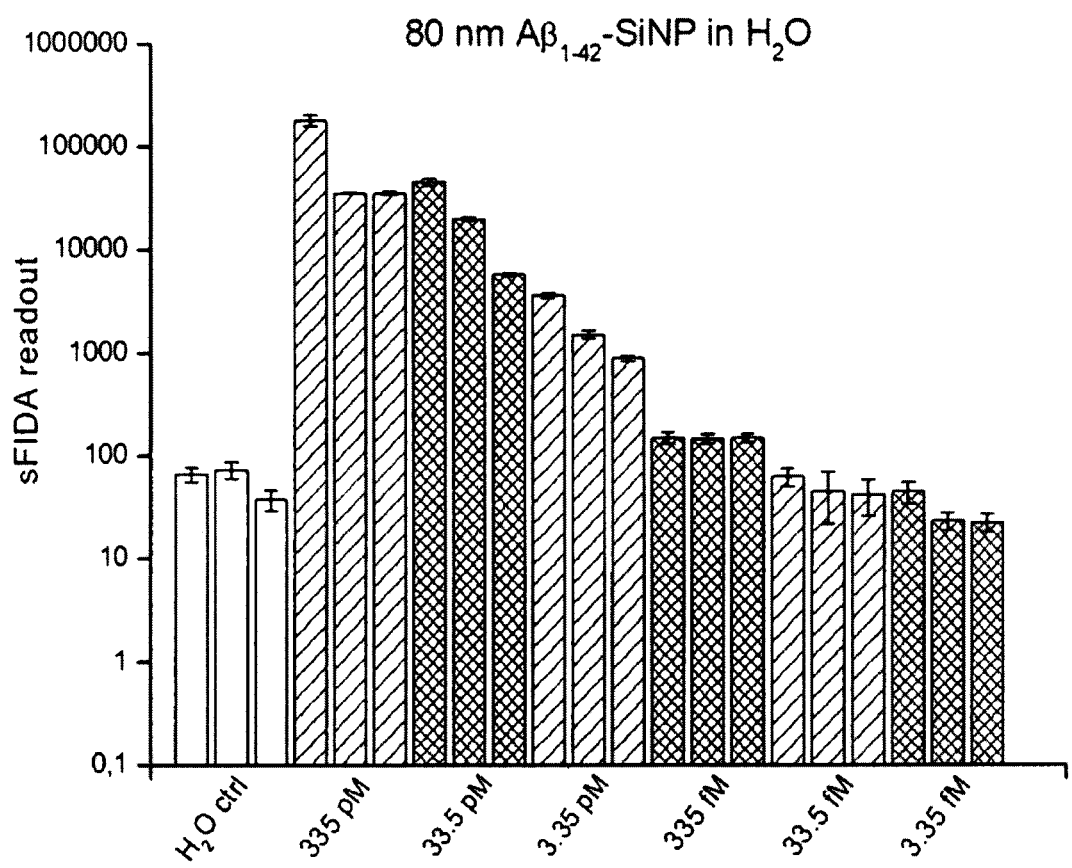
FIG. 5 shows a sFIDA readout for a serial dilution of 80 nm large $A\beta_{1\text{-}42}$ SiNP in H2O.

FIG. 5 shows the sFIDA readout for a serial dilution of 80 nm large $A\beta_{1-42}$ SiNP in $H_2O$. This shows a clear correlation between the $A\beta_{1-42}$ SiNP concentration and the sFIDA readout.

Figure 6:
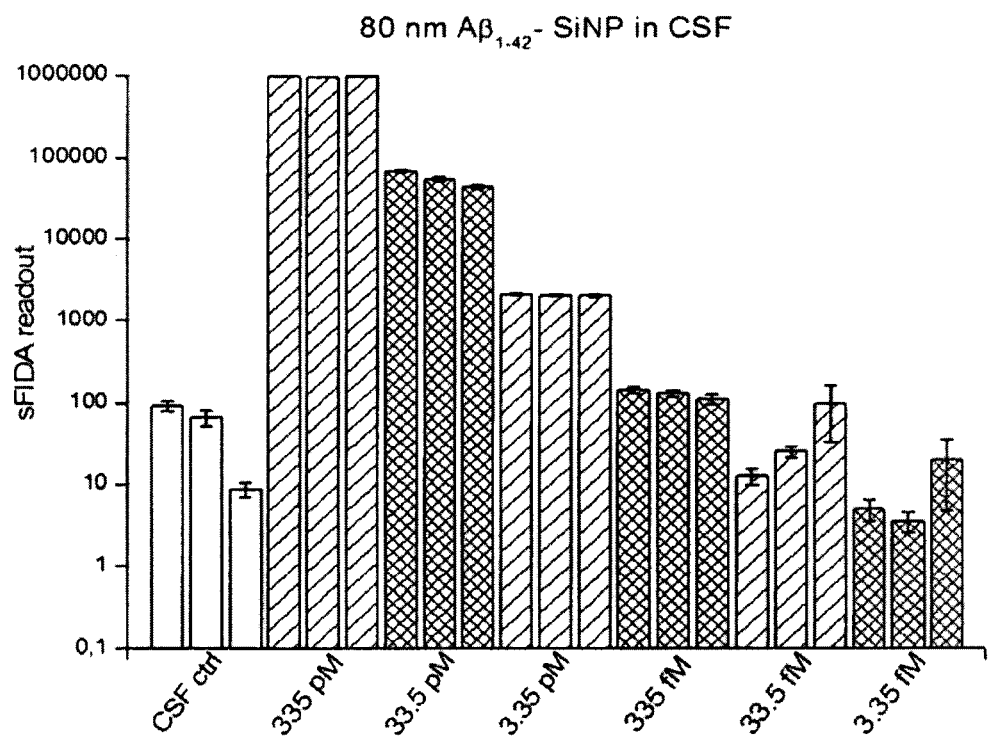
FIG. 6 shows a sFIDA readout for a serial dilution of 80 nm large $A\beta_{1\text{-}42}$ SiNP in CSF.

FIG. 6 shows the sFIDA readout for a serial dilution of 80 nm large $A\beta_{1-42}$ SiNP in CSF. This shows a clear correlation between the $A\beta_{1-42}$ SiNP concentration and the sFIDA readout.

Figure 7:
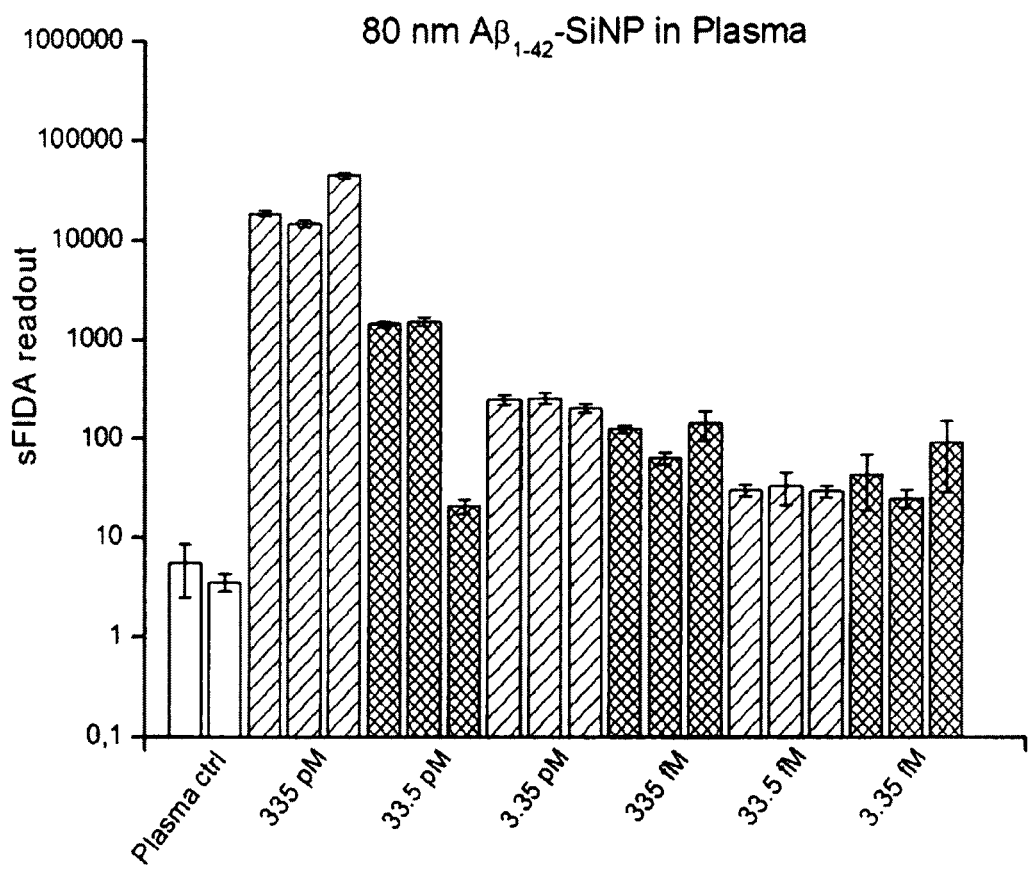
FIG. 7 shows a sFIDA readout for a serial dilution of 80 nm large $A\beta_{1\text{-}42}$ SiNP in plasma.
Figure 8:
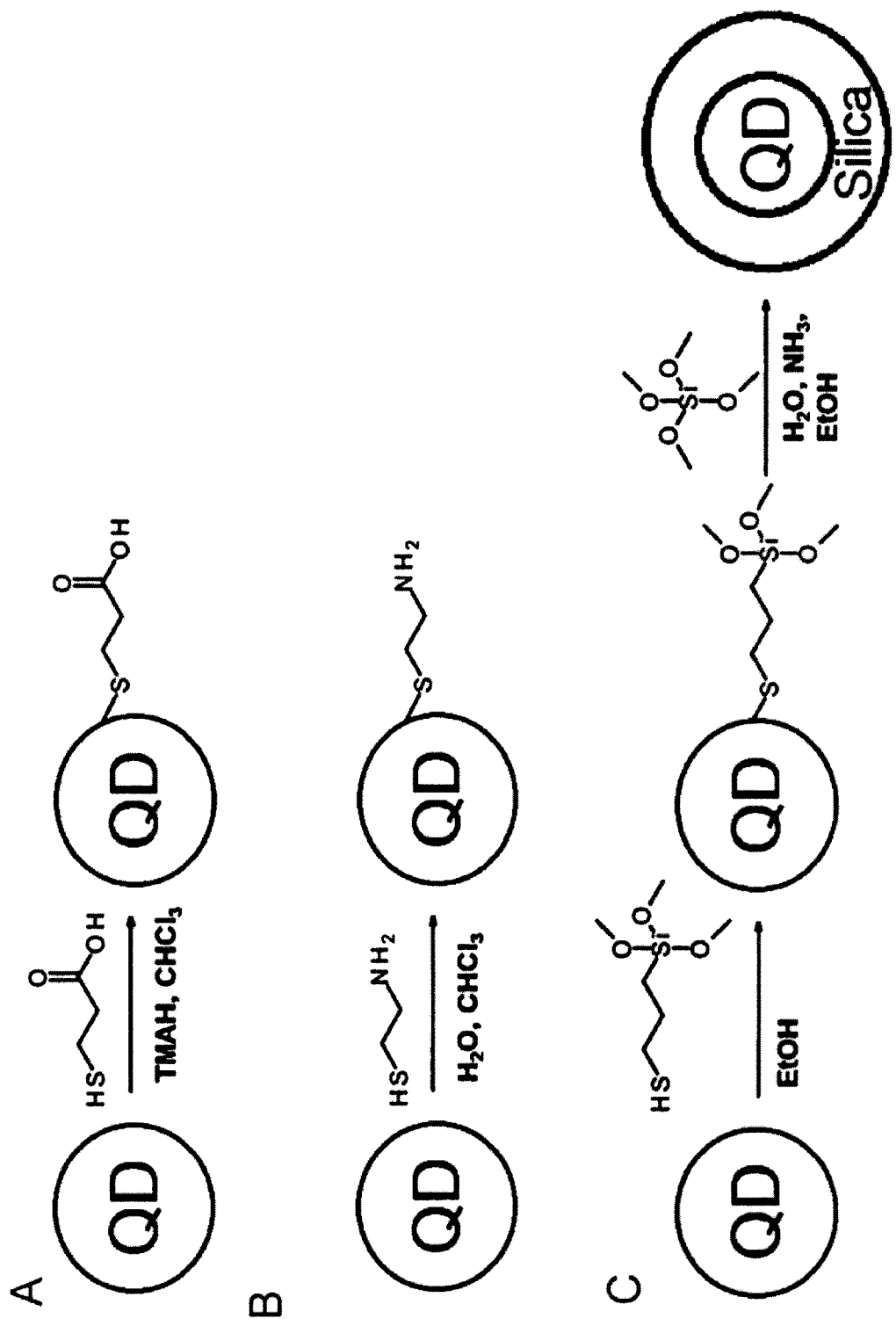
FIG. 8 shows the surface functionalization of CdSe/ZnS quantum dots.

FIG. 7 shows the sFIDA readout for a serial dilution of 80 nm large $A\beta_{1-42}$ SiNP in plasma. This shows a clear correlation between the $A\beta_{1-42}$ SiNP concentration and the sFIDA readout, and a clear delimitation of the signal from the plasma control.

FIG. 8 shows:

A The surface functionalization of CdSe/ZnS quantum dots with 3-mercaptopropionic acid, which results in a carboxy-functionalized quantum dot.

B The surface functionalization of CdSe/ZnS quantum dots with 2-mercaptoethylamine, which results in an amino-functionalized nanoparticle.

C The surface functionalization of CdSe/ZnS quantum dots with (3-mercaptopropyl)trimethoxysilane, which results in a silanized quantum dot. This can subsequently be surrounded with a silicate shell by way of the Stöber process.

The method for producing a standard for detecting the protein aggregates and for oligomers of a protein misfolding disease is performed by way of the following steps:

A) providing an inorganic nanoparticle having the size of the protein aggregate and/or of the oligomer of a protein misfolding disease to be detected;

B) coupling recognition sequences (three variants

Variant 1. Coupling Recognition Sequences to Primary Amines i. forming free amino groups or carboxyl groups on the surface of the nanoparticle for functionalizing the nanoparticle surface into an amine- or carboxy-functionalized nanoparticle;

ii. optionally: converting the free amino groups into carboxyl groups;

iii. converting the carboxyl groups on the surface of the nanoparticles into an NHS ester;

iv. binding amino groups of monomers of the potentially toxic aggregate and/or oligomer of the protein misfolding disease to the NHS esters from step iii).

v.

Variant 2. Coupling Recognition Sequences to Thiols i. forming free amino groups or carboxyl groups on the surface of the nanoparticle for functionalizing the nanoparticle surface into an amino-functionalized nanoparticle;

ii. coupling a carboxy spacer maleimide molecule to the primary amine;

iii. binding thiol groups of the recognition sequence or of the oligomer peptide of the protein misfolding disease to the maleimide group from step ii).

Variant 3.

i. forming free amino groups on the surface of the nanoparticle for functionalizing the nanoparticle surface into an amino-functionalized nanoparticle;

ii. forming free amino groups or carboxyl groups on the surface of the nanoparticle for functionalizing the nanoparticle surface into an amine- or carboxy-functionalized nanoparticle:

iii. optionally: converting the free amino groups into carboxyl groups;

iv. converting the carboxyl groups on the surface of the nanoparticles into an NHS ester;

v. binding amino groups of streptavidin to the NHS esters from step iv);

vi. binding a biotinylated recognition sequence of the protein misfolding disease to the streptavidin molecules.

Definitions of Terms

Within the meaning of the invention, the following terms shall be understood to mean the following:

Epitope is an immunology term referring to a region on the surface of an antigen to which antibodies can bind.

Antigen an immunology term referring to a molecule that is considered foreign by the immune system.

In chemistry, an acyl group, acyl or alkanoyl refers to a functional group having the general formula R—(C=O)—, where R is an organyl group (alkyl, aryl or a heteroaromatic group and the like), or a hydrogen atom.

Imides (imido compounds) are a substance group of organic compounds, comprising the functional group R—C(O)—NR—C(O)—R, which is to say diacylamides.

Succinimide is a chemical compound from the group of the carboxylic acid imides, and the imide of succinic acid.

N-hydroxysuccinimide (NHS, usually abbreviated as HOSu in chemical formulas, according to IUPAC: 1-hydroxy-2,5-pyrrolidinedione) is the N-hydroxy derivative of succinimide. The substance is used in organic systems above ail to produce so-called NHS esters. NHS esters are "activated carboxylic acids" and react easily with amino functional groups—such as those of peptides or proteins—which are considerably more nucleophilic than alcohols.

The invention claimed is:

1. A method of using a standard for the detection of a protein aggregate of Alzheimer's disease, comprising:

providing an inorganic silica nanoparticle having the size 15 to 200 nm;

forming free amino groups on the surface of the inorganic silica nanoparticle for functionalizing the inorganic silica nanoparticle surface into an amine-functionalized nanoparticle;

binding a maleinimido spacer carboxylic acid to the free amino groups;

binding an amyloid beta monomer of the protein aggregate to the maleinimido spacer carboxylic acid by way of a sulfhydryl group at a free end of the amyloid beta monomer of the protein aggregate, thereby producing the standard comprising a known number of binding sites;

providing a sample comprising an unknown number of binding sites;

treating the sample and the standard with a fluorescent-labeled antibody; and inferring the number of binding sites in the sample from the standard treated with said fluorescent-labeled antibody.

\* \* \* \* \*